United States Patent
Takahashi et al.

(10) Patent No.: US 7,683,169 B2
(45) Date of Patent: Mar. 23, 2010

(54) CRYSTALS OF PHENYLALANINE DERIVATIVES AND PRODUCTION METHODS THEREOF

(75) Inventors: Shinichiro Takahashi, Kawasaki (JP); Noriyasu Kataoka, Kawasaki (JP); Akinori Tatara, Kawasaki (JP); Toshihiro Matsuzawa, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 853 days.

(21) Appl. No.: 11/441,106

(22) Filed: May 26, 2006

(65) Prior Publication Data

US 2007/0018172 A1    Jan. 25, 2007

Related U.S. Application Data

(63) Continuation of application No. PCT/JP2004/017708, filed on Nov. 29, 2004.

(30) Foreign Application Priority Data

Nov. 27, 2003    (JP) .............................. 2003-397347

(51) Int. Cl.
C07D 239/72    (2006.01)
(52) U.S. Cl. ..................................... 544/283
(58) Field of Classification Search .................. 544/283
See application file for complete search history.

(56) References Cited

U.S. PATENT DOCUMENTS

| | | |
|---|---|---|
| 6,479,078 B1 | 11/2002 | Hedström et al. |
| 6,552,189 B2 | 4/2003 | Iishi et al. |
| 6,610,710 B2 | 8/2003 | Tanaka et al. |
| 7,105,520 B2 | 9/2006 | Suzuki et al. |
| 7,193,108 B2 | 3/2007 | Chiba et al. |
| 7,250,516 B2 | 7/2007 | Okuzumi et al. |
| 2003/0220268 A1 | 11/2003 | Makino et al. |
| 2003/0220318 A1 | 11/2003 | Suzuki et al. |
| 2005/0101779 A1 | 5/2005 | Sagi et al. |
| 2005/0222141 A1 | 10/2005 | Sagi et al. |
| 2006/0009476 A1 | 1/2006 | Kataoka et al. |
| 2006/0223836 A1 | 10/2006 | Makino et al. |
| 2008/0108637 A1 | 5/2008 | Fujita et al. |

FOREIGN PATENT DOCUMENTS

| | | |
|---|---|---|
| JP | 5-155821 | 6/1993 |
| WO | 98/39305 | 9/1998 |
| WO | 01/02426 | 1/2001 |
| WO | 01/38330 | 5/2001 |
| WO | 01/44231 | 6/2001 |
| WO | 02/16329 | 2/2002 |
| WO | WO 02/16329 A1 * | 2/2002 |
| WO | 02/26709 | 4/2002 |
| WO | 03/070709 | 8/2003 |
| WO | 2004/074264 | 9/2004 |
| WO | 2005/046696 | 5/2005 |
| WO | 2005/046697 | 5/2005 |

OTHER PUBLICATIONS

Haleblian et al., "Characterization of Habits and Crystalline . . . ", J'nal Pharm. Sci, Aug. 1975, vol. 64, No. 8, p. 1269-1288.*
U.S. Appl. No. 11/963,144, filed Dec. 21, 2007, Sagi, et al.
U.S. Appl. No. 11/767,969, filed Jun. 25, 2007, Sagi, et al.
U.S. Appl. No. 11/430,284, filed May 9, 2006, Makino, et al.
M. Matsumoto et al, Manual of pharmaceutics (Yakuzaigaku), Mar. 20, 1989, pp. 28-29 and 76-77 (with attached English excerpt).
U.S. Appl. No. 11/433,589, filed May 15, 2006, Higuchi, et al.
U.S. Appl. No. 11/433,618, filed May 15, 2006, Ogawa, et al.
J. Haleblian, "Characterization of Habits and Crystalline Modification of Solids and Their Pharmaceutical Applications", *Journal of Pharmaceutical Sciences*, Aug. 1975, vol. 64, No. 8, pp. 1269-1288.
"Jikken Kagaku Kohza (vol. 1) Kihon Sosa I, Fourth Edition", *The Chemical Society of Japan*, Nov. 5, 1990, pp. 184-186 (with attached English excerpt).
M. Hashida, "Keiko Toyo Seizai no Sekkei to Hyoka", Feb. 10, 1995, pp. 76-79 and pp. 171-172 (with attached English excerpt).
M. Matsumoto e al, Manual of pharmaceutics (Yakuzaigaku), Mar. 20, 1989, pp. 28-29 and p. 76 (with attached English excerpt).
C. Wermuth et al, "Introduction", *Handbook of Pharmaceutical Salts, Properties, Selection, and Use*, pp. 1-7.
D. Giron et al, "Chapter 3, Evaluation of Solid-State Properties of Salts", *Handbook of Pharmaceutical Salts, Properties, Selection, and Use*, pp. 41-81.
S. Lee, "Large-Scale Aspects of Salt Formation: Processing of Intermediates and Final Products", *Handbook of Pharmaceutical Salts, Properties, Selection, and Use*, pp. 191-220.
U.S. Appl. No. 12/470,846, filed May 22, 2009, Kataoka, et al.

* cited by examiner

*Primary Examiner*—James O. Wilson
*Assistant Examiner*—Paul V. Ward
(74) *Attorney, Agent, or Firm*—Oblon, Spivak, McClelland, Maier & Neustadt, L.L.P.

(57) ABSTRACT

The present invention provides crystals of phenylalanine derivatives of the formula (I):

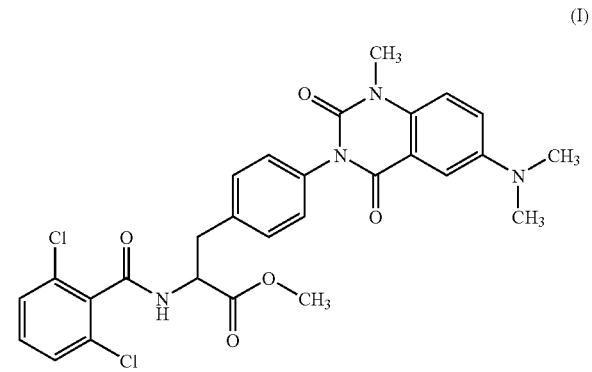

and particularly α-type, γ-type, ε-type, η-type, and θ-type crystals thereof. These crystals are excellent in preservation stability or moisture resistance. They can also be produced on an industrial scale.

15 Claims, 12 Drawing Sheets

CRYSTALS OF PHENYLALANINE DERIVATIVES AND PRODUCTION METHODS THEREOF

CROSS REFERENCES TO RELATED APPLICATIONS

This application is a continuation of International Patent Application No. PCT/JP2004/017708, filed on Nov. 29, 2004, and claims priority to Japanese Patent Application No. 2003-397347, filed on Nov. 27, 2003, both of which are incorporated herein by reference in their entireties.

BACKGROUND OF THE INVENTION

1. Field of the Invention

The present invention relates to crystals of phenylalanine derivatives that have the specific structural formula. The present method also relates to methods for making such crystals.

2. Discussion of the Background

Compounds of the following formula (I) (hereinafter referred to as compound (I)) or pharmaceutically acceptable salts thereof exhibit α4 integrin inhibiting activity and are useful as agents for treating inflammatory bowel diseases and the like. Though they can be produced in accordance with the description of WO02/16329, there is no disclosure of any "crystals" of compound (I) or pharmaceutically acceptable salts thereof in the publication.

Generally, when preserving drug substances or processing or preserving preparations, amorphous or noncrystalline solid drug substances are unstable in the environmental conditions such as temperature, humidity, air, and the like. Therefore, amorphous or noncrystalline solid drug substances can be problematic in developing highly-pure pharmaceutical compositions. Further, since amorphous or noncrystalline solid drug substances are degradable by moisture absorption, the solvents that can be used in processing preparations are limited to those which are anhydrous and, therefore, it can cause an increase in preparation costs. In addition, the drug substances have to be those that can be produced on the industrial scale.

SUMMARY OF THE INVENTION

Accordingly, it is one object of the present invention to provide novel crystals of the compound (I) that are excellent in preservation stability and/or moisture resistance.

It is another object of the present invention to provide novel crystals of the compound (I) which can be produced on an industrial scale.

The inventors have thoroughly studied the above problems to solve them and researched crystal forms of compound (I) or pharmaceutically acceptable salts thereof. Then, they have surprisingly found that compound (I) itself which does not form a salt is excellent in stability or crystallization. The inventors have also found five novel crystal forms to solve the above problems from several crystal forms of the compound (I). The present invention has been completed based on these findings.

Thus, the present invention provides the following:

1. A crystal of a compound of formula (I):

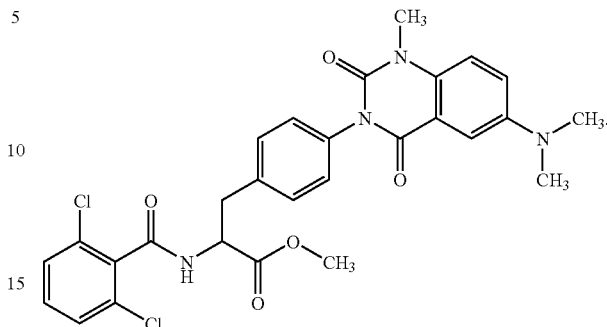

(2) A crystal according to above (1), which is an α-type, γ-type, ε-type, η-type, or θ-type crystal.

(3) A method for producing an α-type crystal of a compound of formula (I), which comprises the steps of: dissolving a compound of a formula (I) in a good solvent(s) which comprises at least one solvent selected from the group consisting of acetonitrile, dichloromethane, tetrahydrofuran, acetone, dimethylsulfoxide, chloroform, and mixtures thereof or in a mixed solvent of acetonitrile-water, or in a mixed solvent of acetonitrile-dimethylformamide; and cooling the mixture to 0 to 30° C. to crystallize.

(4) A method for producing an α-type crystal of a compound of formula (I) which comprises dissolving a compound of the formula (I) in a good solvent(s) and then adding a poor solvent(s) thereto to crystallize, wherein the combination of the good solvent(s) and the poor solvent(s) is either one of dimethylsulfoxide-toluene, dimethylformamide-diethylether, dimethylformamide-toluene, chloroform-ethanol, chloroform-toluene, chloroform-diethylether, dichloromethane-diethylether, tetrahydrofuran-water, tetrahydrofuran-cyclohexane, acetone-water, acetonitrile-water, or dimethylformamide-acetonitrile.

(5) A method for producing an α-type crystal of a compound of formula (I) which comprises: suspending a compound of the formula (I) in acetonitrile, a mixed solvent of acetonitrile-water, or a mixed solvent of acetonitrile-dimethylformamide; and stirring the mixture at 0 to 40° C. to crystallize.

(6) A method for producing a γ-type crystal of a compound of formula (I) which comprises dissolving a compound of the formula (I) in dimethylformamide and then cooling the mixture to 0 to 30° C. to crystallize.

(7) A method for producing a γ-type crystal of a compound of formula (I) which comprises dissolving a compound of the formula (I) in a good solvent(s) and then adding a poor solvent(s) thereto to crystallize, wherein the combination of the good solvent(s) and the poor solvent(s) is dimethylformamide-water.

(8) A method for producing a ε-type crystal of a compound of formula (I) which comprises dissolving a compound of formula (I) in a good solvent(s) and then adding a poor solvent(s) thereto to crystallize, wherein the combination of the good solvent(s) and the poor solvent(s) is either one of dichloromethane-ethanol or dimethylsulfoxide-diethylether.

(9) A method for producing an η-type crystal of a compound of formula (I) which comprises: dissolving a compound of formula (I) or a hydrochloride of said compound of the formula (I) in an alcohol solution having 1 to 6 carbon atoms containing hydrogen chloride; and then neutralizing the mixture with a base(s) to crystallize.

(10) A method for producing a θ-type crystal of a compound of formula (I) which comprises: suspending a compound of formula (I) in a mixed solvent of dimethylformamide-acetonitrile or in a mixed solvent of acetonitrile-water; and stirring the mixture at 40° C. or higher to crystallize.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
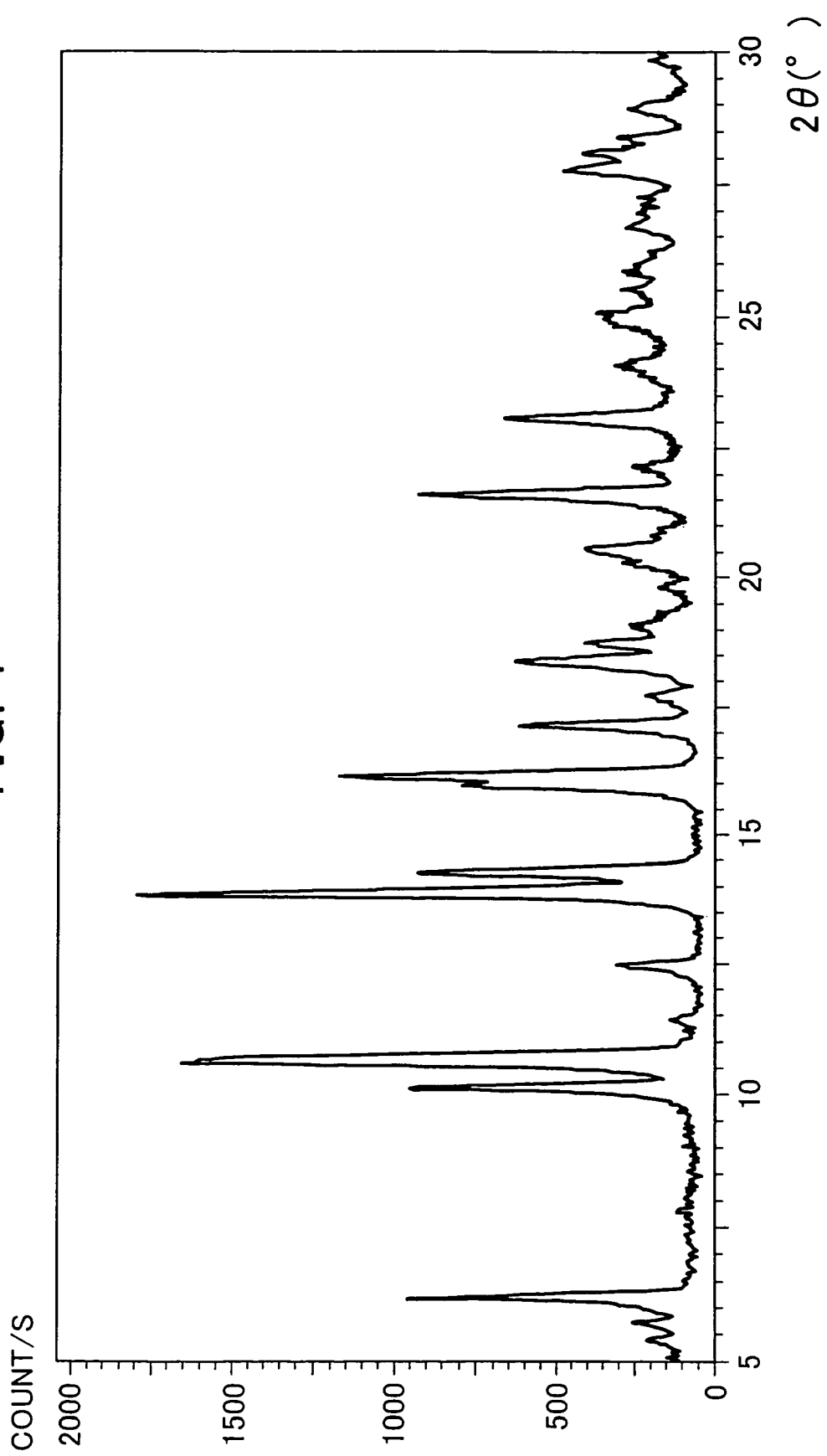
FIG. 1 is a powder X-ray diffraction pattern of the novel α-type crystal of the present invention. The horizontal axis indicates the diffraction angle 2θ (°); and the vertical axis indicates the strength (counts per second, CPS).
Figure 2:
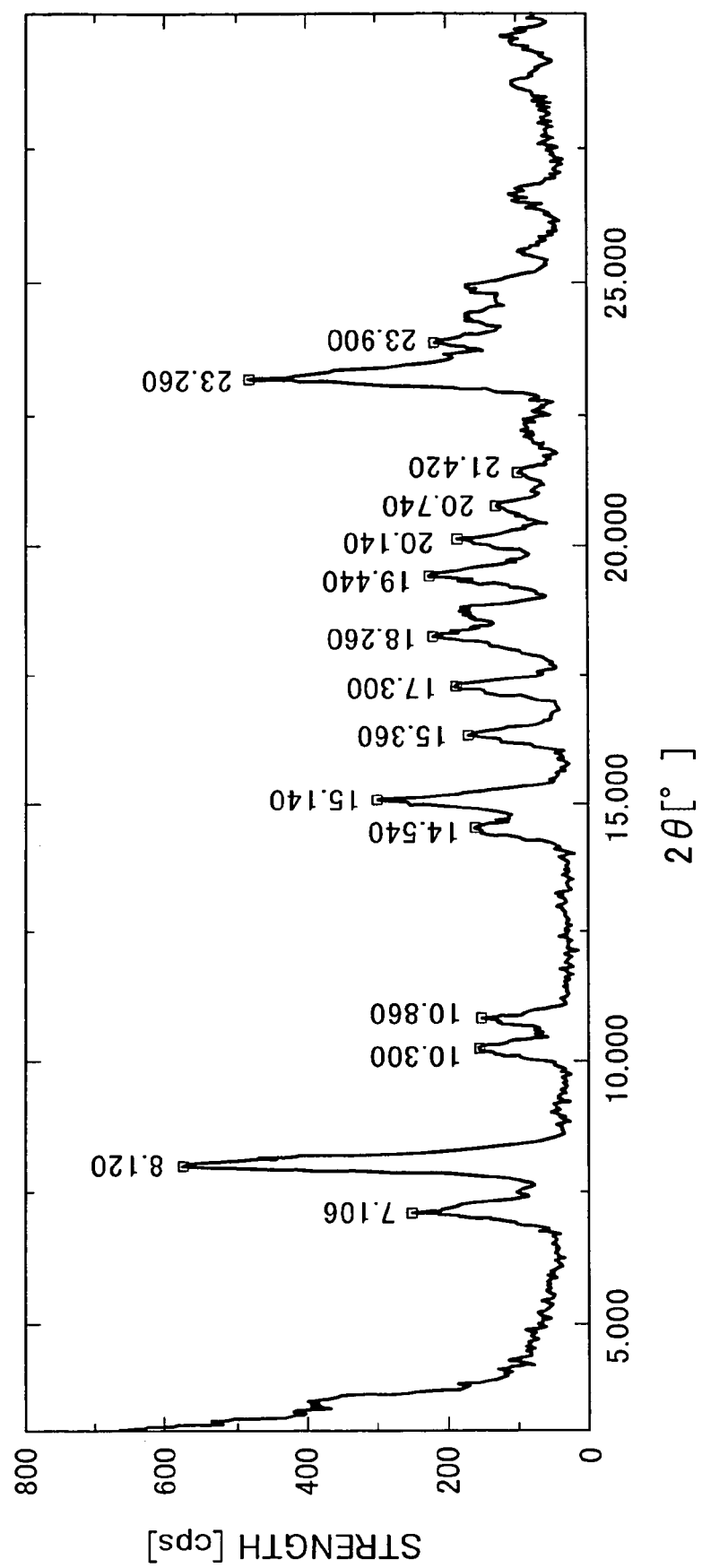
FIG. 2 is a powder X-ray diffraction pattern of the novel γ-type crystal of the present invention. The horizontal axis indicates the diffraction angle 2θ (°); and the vertical axis indicates the strength (counts per second, CPS).
Figure 3:
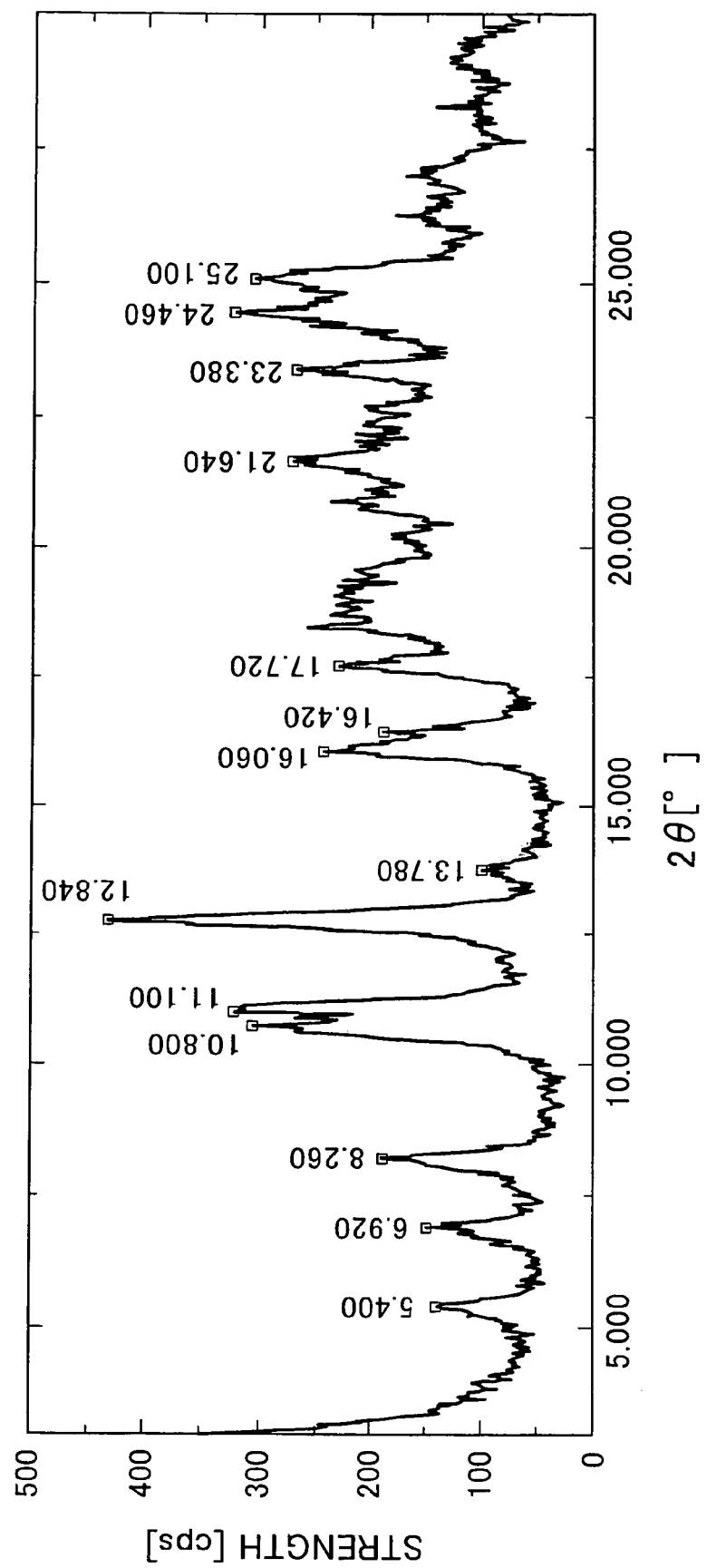
FIG. 3 is a powder X-ray diffraction pattern of the novel ε-type crystal of the present invention. The horizontal axis indicates the diffraction angle 2θ (°); and the vertical axis indicates the strength (counts per second, CPS).
Figure 4:
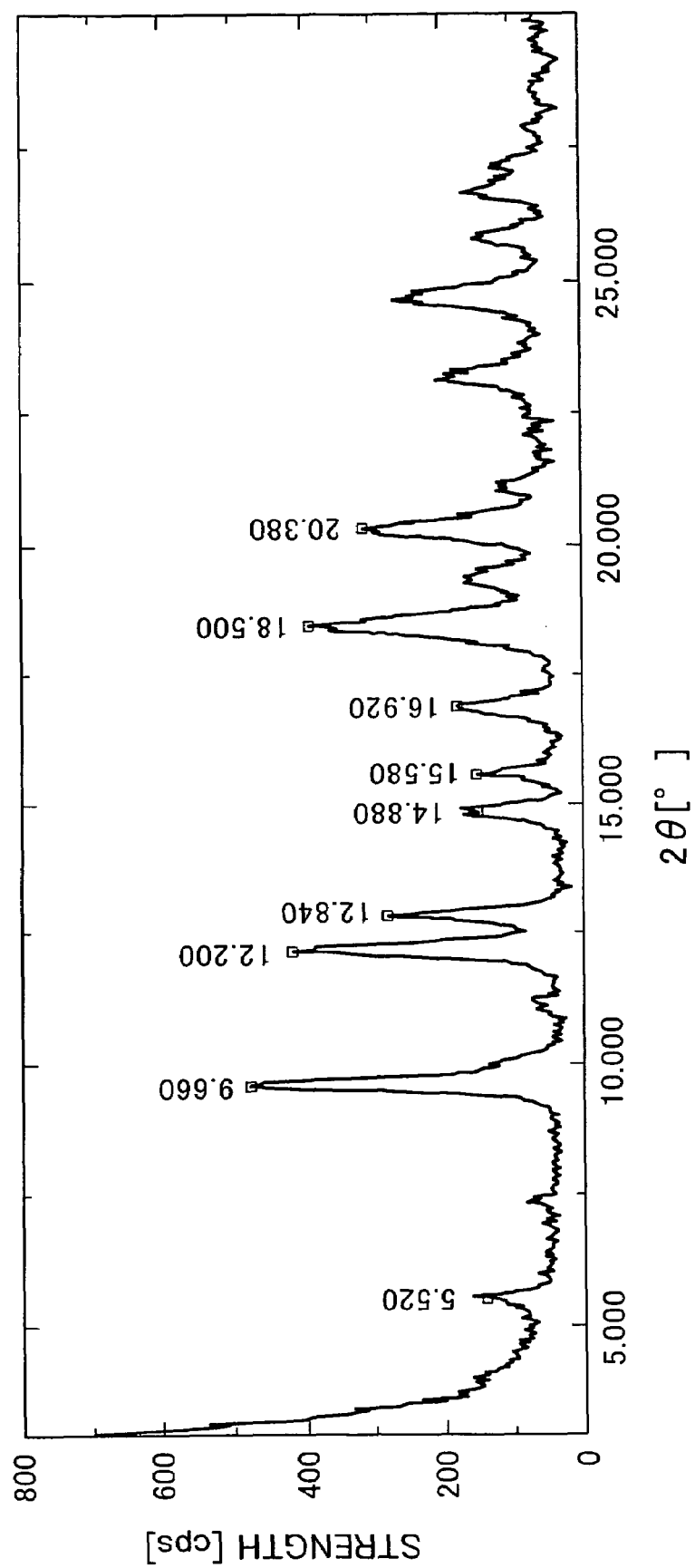
FIG. 4 is a powder X-ray diffraction pattern of the novel η-type crystal of the present invention. The horizontal axis indicates the diffraction angle 2θ (°); and the vertical axis indicates the strength (counts per second, CPS).
Figure 5:
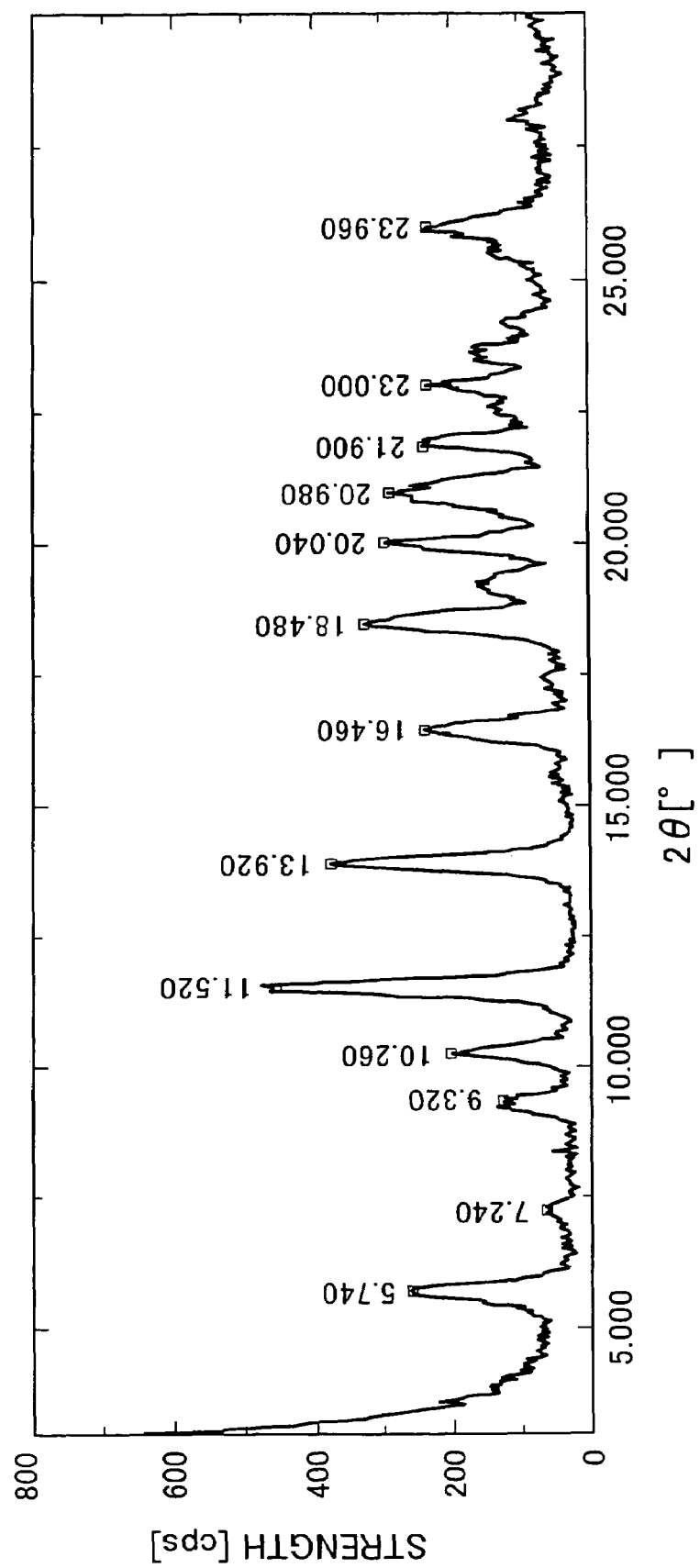
FIG. 5 is a powder X-ray diffraction pattern on the novel θ-type crystal of the present invention. The horizontal axis indicates the diffraction angle 2θ (°); and the vertical axis indicates the strength (counts per second, CPS).

The definitions or examples in the present specification are indicated as follows.

"The compound of the formula (I)" is the compound described in Example 196 of WO02/16329.

The term "crystal" mean a solid substance that gives a characteristic diffraction diagram in the powder X-ray analysis and usually mean crystals or crystalline solids. Further, the term "crystal" also includes mixtures of a crystalline form and amorphous form. In such a case, the crystals may be contained in a substantial amount. When in a mixture with an amorphous form, the crystal of the present invention preferably comprises at least 50% by weight, more preferably at least 75% by weight, more preferably at least 90% by weight, more preferably at least 95% by weight, more preferably at least 97% by weight, more preferably at least 99% by weight, based on the total weight of the crystalline form and the amorphous form.

The term "α-type crystal" means the crystal wherein peaks exist at the diffraction angles (2θ) of at least 6.2, 10.7, and 14.0° in the powder X-ray diffraction pattern. In another embodiment, the term "α-type crystal" means the crystal wherein peaks exist at the diffraction angles (2θ) of at least 10.7, 10.8, 14.0, 16.2, and 21.7° in the powder X-ray diffraction pattern. Particularly, it means the crystal wherein peaks exist at the diffraction angles (2θ) of at least 6.2, 10.2, 10.7, 10.8, 14.0, 14.4, 16.0, 16.2, and 21.7°.

The term "γ-type crystal" means the crystal wherein peaks exist at the diffraction angles (2θ) of at least 7.2, 8.1, 15.1, and 23.3° in the powder X-ray diffraction pattern. Particularly, it means the crystal wherein peaks exist at the diffraction angles (2θ) of at least 7.2, 8.1, 10.3, 10.9, 14.5, 15.1, 16.4, 17.3, 18.3, 19.4, and 23.3° in the powder X-ray diffraction pattern.

The term "ε-type crystal" means the crystal wherein peaks exist at the diffraction angles (2θ) of at least 8.3, 11.1, 12.8, 16.1, and 24.5° in the powder X-ray diffraction pattern. Particularly, it means the crystal wherein peaks exist at the diffraction angles (2θ) of at least 5.4, 6.9, 8.3, 10.8, 11.1, 12.8, 16.1, 17.7, 21.6 23.4, 24.5, and 25.1° in the powder X-ray diffraction pattern.

The term "η-type crystal" means the crystal wherein peaks exist at the diffraction angles (2θ) of at least 9.7, 12.2, 18.5, 20.4° in the powder X-ray diffraction pattern. Particularly, it means the crystal wherein peaks exist at the diffraction angles (2θ) of at least 9.7, 12.2, 12.8, 14.9, 15.6, 16.9, 18.5, and 20.4° in the powder X-ray diffraction pattern.

The term "θ-type crystal" means the crystal wherein peaks exist at the diffraction angles (2θ) of at least 5.7, 11.5, and 13.9° in the powder X-ray diffraction pattern. In another embodiment, the term "θ-type crystal" means the crystal wherein peaks exist at the diffraction angles (2θ) of at least 11.5, 13.9, 18.5, 20.0, and 21.0° in the powder X-ray diffraction pattern. Particularly, it means the crystal wherein peaks exist at the diffraction angles (2θ) of at least 5.7, 10.3, 11.5, 13.9, 16.5, 18.5, 20.0, and 21.0°.

In the production methods of the present invention, in addition to using amorphous or noncrystalline solids as the compound (I), the raw material, the amorphous or noncrystalline solids may be used to once prepare crystals, and then other crystals may be produced using the obtained crystals in accordance with the other production methods of the present invention.

The used crystallization processes include, for example, the crystallization by cooling, the crystallization with a poor solvent(s), the crystallization by suspension, the crystallization by neutralization, and the crystallization by concentration. Any process can be conducted if the subject compound is dissolved or suspended to a crystallizing solvent(s) to crystallize. In the crystallization, a seed crystal(s) is preferably added to the mixture. Meanwhile, the crystallization by cooling and the crystallization with a poor solvent(s) may be combined together.

The crystallizing solvents are those that are usually known as usable crystallizing solvents. They may be one kind or a mixed solvent(s) of several crystallizing solvents.

As for the mixed solvents of the several crystallizing solvents, it is possible to use the mixed solvent(s) wherein the solvent that dissolves the subject compound well (a good solvent) and the solvent that is soluble in the good solvent but hardly dissolves the subject compound (a poor solvent) are mixed in suitable quantities. It is also possible to use several solvents as the good solvent and those as the poor solvent. In that case, it is preferable that they equally intermingle with each other.

The solvents that dissolve the subject compound (the compound of the formula (I)) well can be used as "the good solvents." They include acetonitrile, tetrahydrofuran, acetone, chloroform, dichloromethane, dimethylformamide, formamide, and dimethylsulfoxide.

The solvents that are soluble in the above good solvents but hardly dissolve the subject compound (the compound of the formula (I)) can be used as "the poor solvents." They include water; alcohols such as methanol, ethanol and octanol; ethers such as diethylether; esters of acetic acids such as ethyl acetate; and hydrocarbons such as toluene, cyclohexane and hexane.

In case of the crystallization by cooling, the key is to once dissolve the compound in the good solvent(s), the mixed solvent(s) of the good solvents, or the mixed solvent(s) of the good solvent(s) and the poor solvent(s), and then to cool down the mixture to precipitate the crystals of the subject compound. In order to once dissolve it, heating is preferable and the heating temperature is within the range from 30° C. to around the boiling point of the solvent.

For example, when precipitating the α-type crystal, it is preferable to dissolve the compound of the formula (I) in a good solvent(s) containing at least one kind selected from acetonitrile, dichloromethane, tetrahydrofuran, acetone, dimethylsulfoxide and chloroform, or in a mixed solvent of acetonitrile-water, or in a mixed solvent of acetonitrile-dimethylformamide; and then cool down the mixture to 0 to 30° C. and more preferably 4 to 25° C. to crystallize.

In the above, the volume ratio of acetonitrile in the mixed solvent of acetonitrile-water is preferably within the range from 50 to less than 100 v/v %, and more preferably from 80 to 99 v/v %.

When precipitating the γ-type crystal, it is preferable to dissolve the compound of the formula (I) in dimethylformamide and then cool down the mixture to 0 to 30° C. and more preferably 4 to 25° C. to crystallize.

In case of the crystallization with a poor solvent(s), the key is the selection of the good solvents and the poor solvents or the used quantities thereof. The crystals of the subject compound are precipitated by adding the poor solvent(s) to the good solvent(s). As for the selection of the used solvents or the used quantities thereof, the most suitable condition can be selected by the experiments on solubility.

For example, when precipitating the α-type crystal, it is preferable to dissolve the compound of the formula (I) in a good solvent(s) and then adding a poor solvent(s) thereto to crystallize, wherein the combination of the good solvent(s) and the poor solvent(s) is either one of dimethylsulfoxide-toluene, dimethylformamide-diethylether, dimethylformamide-toluene, chloroform-ethanol, chloroform-toluene, chloroform-diethylether, dichloromethane-diethylether, tetrahydrofuran-water, tetrahydrofuran-cyclohexane, acetone-water, acetonitrile-water or dimethylformamide-acetonitrile. In these combinations, the good solvent(s)/the poor solvent(s) is preferably used in 1/20 to 5/1 (volume ratio).

Meanwhile, depending on the combinations of the good solvents, the above includes addition of the other good solvent(s) to the above good solvent(s) to precipitate the crystals of the subject compound.

For instance, when precipitating the α-type crystal, it includes the method comprising the steps of: dissolving the compound of the formula (I) in dimethylformamide under heating (e.g. 30 to 80° C.); adding dropwise 1 to 20 times volume and more preferably 2 to 8 times volume of acetonitrile to the dissolution solution at 0 to 80° C. to crystallize.

When precipitating the γ-type crystal, it is preferable to dissolve the compound of the formula (I) in a good solvent(s) and then add a poor solvent(s) thereto to crystallize, wherein the combination of the good solvent(s) and the poor solvent(s) is dimethylformamide-water. In this case, dimethylformamide/water is preferably used in 50/1 to 1000/1 (volume ratio).

Besides, when precipitating the ε-type crystal, it is preferable to dissolve the compound of the formula (I) in a good solvent(s) and then add a poor solvent(s) thereto to crystallize, wherein the combination of the good solvent(s) and the poor solvent(s) is either one of dichloromethane-ethanol or dimethylsulfoxide-diethylether. In these combinations, the good solvent(s)/the poor solvent(s) is preferably used in 1/5 to 1/2 (volume ratio).

The crystallization by suspension includes the method which comprises the steps of: suspending the compound of the formula (I) in either one of acetonitrile, a mixed solvent of acetonitrile-water, or a mixed solvent of acetonitrile-dimethylformamide; and stir the mixture to crystallize. In case of using the mixed solvent(s), acetonitrile-water or acetonitrile-dimethylformamide is preferably used in 50/50 to 95/5 (volume ratio).

When obtaining the α-type crystal, in case of using acetonitrile-water (90/10: volume ratio) as a suspending solvent, it is preferable to suspend the amorphous or the crystals (here, the crystals mean various crystal forms) of the compound of the formula (I) in the solvent, stir the mixture at 0 to 30° C. and isolate the crystals at 0 to 30° C. (e.g. at room temperature) by filtration. At that time, the subject α-type crystal may be seeded at 0 to 30° C.

Further, when obtaining the α-type crystal, it is preferable to suspend the amorphous or the crystals (here, the crystals mean various crystal forms) of the compound of the formula (I) at 0 to 40° C. (e.g. at room temperature) in acetonitrile-dimethylformamide (80/20: volume ratio), stir the mixture at 0 to 40° C. and isolate the crystals at 0 to 40° C. (e.g. at room temperature) by filtration. At that time, the subject α-type crystal may be seeded at 0 to 40° C.

On the other hand, when obtaining the θ-type crystal, in case of using acetonitrile-water (90/10: volume ratio) as a suspending solvent, it is preferable to suspend the amorphous or the crystals (here, the crystals mean various crystal forms) of the compound of the formula (I) in the solvent, stir the mixture at 40° C. or higher (e.g. 60° C.) and isolate the precipitated crystals at 40° C. or higher (e.g. 60° C.) by filtration. In such a case, the maximum temperature is preferably the boiling point of the solvent or that of the mixed solvent, or lower than it. At that time, the subject θ-type crystal may be seeded at 40 to 60° C.

Besides, when obtaining the θ-type crystal, it is preferable to suspend the amorphous or the crystals (here, the crystals mean various crystal forms) of the compound of the formula (I) in acetonitrile-dimethylformamide (80/20: volume ratio), stir the mixture at 50° C. or higher (e.g. 60° C.) and isolate the precipitated crystals at 50° C. or higher (e.g. 60° C.) by filtering out. In such a case, the maximum temperature is preferably the boiling point of the solvent or that of the mixed solvent or lower than it. At that time, the subject θ-type crystal may be seeded at 50 to 60° C.

The intersection of the saturation solubility curves of the α-type crystal and the θ-type crystal to each solvent system exists at around 30 to 40° C. in acetonitrile-water (90/10: volume ratio) and around 40 to 50° C. in acetonitrile-dimethylformamide (80/20: volume ratio). At around these temperatures, the mixture of the α-type crystal and the θ-type crystal is obtained.

The crystallization by neutralization includes the method comprising the steps of dissolving the compound of the formula (I) or a hydrochloride of the compound of the formula (I) in a lower alcohol solution containing hydrogen chloride; and then neutralizing the mixture with a base(s) to crystallize.

The bases include inorganic bases such as sodium hydroxide and potassium hydroxide and organic bases such as triethylamine.

The alcohol solutions having 1 to 6 carbon atoms include methanol, ethanol, propanol, butanol, pentanol and hexanol. Methanol and ethanol are preferable among them.

The crystals of the present invention are useful in the points that they are the crystals excellent in "preservation stability" or "moisture resistance" of drug substances or preparations; and those that can be produced on the industrial scale.

Especially, since the α-type crystal is thermodynamically most stable under room temperature, it can be easily isolated under room temperature and has low hygroscopicity. Since the θ-type crystal is thermodynamically most stable under high temperature (50° C. or higher), it can be easily isolated under high temperature (50° C. or higher). The η-type crystal is also thermodynamically stable and the γ-type and ε-type crystals are useful in the point of their low hygroscopicity.

All of the α-type, γ-type, ε-type, η-type, and θ-type crystals can be produced on the industrial scale. Particularly, the α-type and θ-type crystals are preferable in terms of the production on the industrial scale.

Other features of the invention will become apparent in the course of the following descriptions of exemplary embodiments which are given for illustration of the invention and are not intended to be limiting thereof.

EXAMPLES

The following Examples will illustrate the production examples of the crystals of the present invention.

The production of the α-type crystal: Examples 1 to 23
The production of the γ-type crystal: Examples 24 and 25
The production of the ε-type crystal: Examples 26 and 27
The production of the η-type crystal: Example 28
The production of the θ-type crystal: Examples 29 to 31

Example 1

The Crystallization by Cooling (the α-type Crystal).

400 mg of the compound of the formula (I) (amorphous, hereinafter same as above unless specifically mentioned otherwise) produced by the production method described in Patent Literature 1 was added to 12 mL of acetonitrile and dissolved by heating at 70° C. The dissolution solution was cooled down to room temperature (about 20 to 30° C., hereinafter same as above). The precipitated crystals were collected by filtration and air-dried to obtain 240 mg of the title crystals.

Example 2

The Crystallization by Cooling (the α-type Crystal).

455 mg of the compound of the formula (I) was added to 3 mL of dichloromethane and dissolved by heating at 40° C. The dissolution solution was cooled down to 4° C. The precipitated crystals were collected by filtration and air-dried to obtain 339 mg of the title crystals.

Example 3

The Crystallization by Cooling (the α-type Crystal).

395 mg of the compound of the formula (I) was added to 20 mL of tetrahydrofuran and dissolved by heating at 70° C. The dissolution solution was cooled down to room temperature. The precipitated crystals were collected by filtration and air-dried to obtain very small quantity of the title crystals.

Example 4

The Crystallization by Cooling (the α-type Crystal).

366 mg of the compound of the formula (I) was added to 46 mL of acetone and dissolved by heating at 50° C. The dissolution solution was cooled down to room temperature. The precipitated crystals were collected by filtration and air-dried to obtain very small quantity of the title crystals.

Example 5

The Crystallization by Cooling (the α-type Crystal).

2539 g of the compound of the formula (I) mainly comprising the α-type crystals were added to 65.9 L of acetonitrile-water (9:1 volume ratio) and dissolved by heating at 68° C. The dissolution solution was cooled down to 50° C (in mid-course seeded at 55° C.) and matured at 50° C. for 2 hours. Then, the crystallization solution was cooled down to 4° C. and stirred overnight. The precipitated crystals were collected by filtration and dried at 60° C. under reduced pressure to obtain 2218 g of the title crystals (yield: 88.5%).

Example 6

The Combination of the Crystallization by Cooling and the Crystallization with a Poor Solvent(s) (the α-type Crystal).

10.06 g of the compound of the formula (I) mainly comprising the α-type crystals were added to 200 mL of acetonitrile-water (9:1 volume ratio) and dissolved by heating at 75° C. The dissolution solution was cooled down to 60° C. and the seed crystals of the α-type crystal were added thereto. The solution was cooled down to 10° C. in 5 hours and the suspension containing the crystals was stirred at 10° C. or lower overnight. Then, 121.4 mL of water was added dropwise to the suspension in 1 hour and matured at 10° C. or lower. The precipitated crystals were collected by filtration, washed with acetonitrile cooled down to 10° C. in advance, and dried at 50° C. under reduced pressure to obtain 9.38 g of the title crystals (yield: 93.8%).

Example 7

The Crystallization with a Poor Solvent(s) (the α-type Crystal).

500 mg of the compound of the formula (I) was dissolved in 1 mL of dimethylsulfoxide. 16 mL of toluene was added to the dissolution solution, and the precipitated crystals were collected by filtration and air-dried to obtain the title crystals (The temperature of the solution before the precipitation: room temperature, hereinafter in Examples 8 to 17 same as above).

Example 8

The Crystallization with a Poor Solvent(s) (the α-type Crystal).

400 mg of the compound of the formula (I) was dissolved in 1 mL of dimethylformamide. 4 mL of diethylether was added to the dissolution solution, and the precipitated crystals were collected by filtration and air-dried to obtain the title crystals.

Example 9

The Crystallization with a Poor Solvent(s) (the α-type Crystal).

400 mg of the compound of the formula (I) was dissolved in 1 mL of dimethylformamide. 8 mL of toluene was added to the dissolution solution, and the precipitated crystals were collected by filtration and air-dried to obtain the title crystals.

Example 10

The Crystallization with a Poor Solvent(s) (the α-type Crystal).

300 mg of the compound of the formula (I) was dissolved in 1.7 mL of chloroform. 3.4 mL of ethanol was added to the dissolution solution, and the precipitated crystals were collected by filtration and air-dried to obtain the title crystals.

Example 11

The Crystallization with a Poor Solvent(s) (the α-type Crystal).

300 mg of the compound of the formula (I) was dissolved in 1.7 mL of chloroform. 2 mL of diethylether was added to the dissolution solution, and the precipitated crystals were collected by filtration and air-dried to obtain the title crystals.

Example 12

The Crystallization with a Poor Solvent(s) (the α-type Crystal).

300 mg of the compound of the formula (I) was dissolved in 1.7 mL of chloroform. 3.4 mL of toluene was added to the dissolution solution, and the precipitated crystals were collected by filtration and air-dried to obtain the title crystals.

Example 13

The Crystallization with a Poor Solvent(s) (the α-type Crystal).

450 mg of the compound of the formula (I) was dissolved in 3 mL of dichloromethane. 4.5 mL of diethylether was added to the dissolution solution, and the precipitated crystals were collected by filtration and air-dried to obtain the title crystals.

Example 14

The Crystallization with a Poor Solvent(s) (the α-type Crystal).

300 mg of the compound of the formula (I) was dissolved in 18 mL of tetrahydrofuran. 15 mL of water was added to the dissolution solution, and the precipitated crystals were collected by filtration and air-dried to obtain the title crystals.

Example 15

The Crystallization with a Poor Solvent(s) (the α-type Crystal).

300 mg of the compound of the formula (I) was dissolved in 18 mL of tetrahydrofuran. 25 mL of cyclohexane was added to the dissolution solution, and the precipitated crystals were collected by filtration and air-dried to obtain the title crystals.

Example 16

The Crystallization with a Poor Solvent(s) (the α-type Crystal).

170 mg of the compound of the formula (I) was dissolved in 22 mL of acetone. 30 mL of water was added to the dissolution solution, and the precipitated crystals were collected by filtration and air-dried to obtain the title crystals.

Example 17

The Crystallization with a Poor Solvent(s) (the α-type Crystal).

300 mg of the compound of the formula (I) was dissolved in 15 mL of acetonitrile. 5 mL of water was added to the dissolution solution, and the precipitated crystals were collected by filtration and air-dried to obtain the title crystals.

Example 18

The Crystallization with a Poor Solvent(s) (the α-type Crystal).

4.85 L of dimethylformamide was added to 2000 g of the compound of the formula (I) mainly comprising the α-type crystals and dissolved by heating at 71° C. 19.4 L of acetonitrile was added dropwise to the dissolution solution at 66 to 75° C. Then, the mixed solution was cooled down to 40° C., the α-type crystals were seeded halfway at 54° C. and matured at 40° C. for 2 hours. Next, the crystallization solution was cooled down to 5° C. in 4 hours and stirred overnight. The precipitated crystals were collected by filtrationt and dried at 60° C. under reduced pressure to obtain 1731 g of the title crystals (yield: 83.0%).

Example 19

The Crystallization by Suspension (the α-type Crystal).

The moist crystal containing 54.8 g of the compound of the formula (I) that is amorphous mainly containing 310.5 g of water was added to 633 mL of acetonitrile, dissolved and stirred at 25° C. for 5.5 hours. The precipitated crystals were isolated by collection by filtration and dried at 60° C. under reduced pressure to obtain 47.4 g of the title crystals (yield: 86%).

Example 20

The Crystallization by Suspension (the α-type Crystal).

32.17 g of the compound of the formula (I) was added to 330 mL of acetonitrile, dissolved and stirred at room temperature for 6 hours. The precipitated crystals were isolated by collected by filtration and dried at 60° C. under reduced pressure to obtain 26.67 g of the title crystals (yield: 83%).

Example 21

The Crystallization by Suspension (the α-type Crystal).

45.0 g of the compound of the formula (I) was added to 112 mL of dimethylformamide and dissolved at 70° C. Keeping the solution temperature at 65° C. or higher, 445 mL of acetonitrile was added dropwise thereto. After adding it dropwise, the dissolution solution was cooled down to 10° C. The crystal obtained by natural crystallization was filtered out and dried at 50° C. under reduced pressure to obtain 36.8 g of the mixture of the α-type crystals and the θ-type crystals (α-type/θ-type=about 1, determined by the powder X-ray strength ratio) (yield: 82%). (When drastically cooling down the solution to conduct the natural crystallization and further filtering out in a short time, the mixture of the α-type crystals and the θ-type crystals is obtained.)

13.42 g of thus obtained mixture of the α-type crystals and the θ-type crystals was added to a solution containing 30 mL of dimethylformamide and 120 mL of acetonitrile, suspended and stirred at 40° C. for 5 hours. Continuously, the mixture was cooled down from 40° C. to 10° C. in 3 hours and matured at 10° C. or lower for 9 hours. The precipitated crystals were collected by filtration, washed with 40 mL of acetonitrile and dried under reduced pressure to obtain 11.63 g of the title crystals (yield: 87%).

Example 22

The Crystallization by Suspension (the α-type Crystal).

The compound of the formula (I) comprising 1.81 g of the α-type crystals and 0.99 g of the θ-type crystals was added to 60 mL of acetonitrile-water (9:1 volume ratio) and stirred at 30° C. for 4 days. At that time, the partial pullout of the suspension was conducted once in order to check the crystal form (0.79 g of the crystals were pulled out). The precipitated crystals were collected by filtration and dried under reduced pressure to obtain 1.17 g of the title crystals.

Example 23

The Crystallization by Suspension (the α-type Crystal).

6.09 g of the compound of the formula (I) comprising the θ-type crystals was added to 120 mL of acetonitrile-water (9:1 volume ratio) and stirred at 10° C. for 24 hours. At that time, the partial pullout of the suspension was conducted five times in order to check the crystal form (total of 3.31 g of the crystals was pulled out). The precipitated crystals were collected by filtration and dried under reduced pressure to obtain 1.36 g of the title crystals.

Example 24

The Crystallization by Cooling (the γ-type Crystal).

530 mg of the compound of the formula (I) was added to 1 mL of dimethylformamide and dissolved by heating at 70° C. Then, the dissolution solution was cooled down to room temperature. The precipitated crystals were collected by filtration and air-dried to obtain 100 mg of the title crystals.

Example 25

The Crystallization with a Poor Solvent(s) (the γ-type Crystal).

Very small quantity of water was added to the dimethylformamide filtrate obtained in Example 20, and the precipitated crystals were collected by filtration and air-dried to obtain the title crystals (The temperature of the solution before the precipitation: room temperature, hereinafter in Examples 26 to 27 same as above).

Example 26

The Crystallization with a Poor Solvent(s) (the ε-type Crystal).

450 mg of the compound of the formula (I) was dissolved in 3 mL of dichloromethane. 9 mL of ethanol was added to the dissolution solution, and the precipitated crystals were collected by filtration and air-dried to obtain the title crystals.

Example 27

The Crystallization with a Poor Solvent(s) (the ε-type Crystal).

500 mg of the compound of the formula (I) was dissolved in 1 mL of dimethylsulfoxide. 4 mL of diethylether was added to the dissolution solution, and the precipitated crystals were collected by filtration and air-dried to obtain the title crystals.

Example 28

The Crystallization by Neutralization (the η-type Crystal).

1.02 g of the compound of the formula (I) was dissolved in 5.0 mL of the hydrogen chloride-methanol solution under room temperature. An aqueous solution of 1M sodium hydroxide was added dropwise thereto, and the precipitated solid was collected by filtration, washed with water and dried under reduced pressure to obtain the title crystals.

Example 29

The Crystallization by Suspension (the θ-type Crystal).

45.0 g of the compound of the formula (I) was added to 112 mL of dimethylformamide and dissolved at 70° C. Keeping the solution temperature at 65° C. or higher, 445 mL of acetonitrile was added dropwise thereto. After adding it dropwise, the dissolution solution was cooled down to 10° C. The crystal obtained by natural crystallization was collected by filtration and dried at 50° C. under reduced pressure to obtain 36.8 g of the mixture of the α-type crystals and the θ-type crystals (α-type/θ-type=about 1, determined by the powder X-ray strength ratio) (yield: 82%). (When drastically cooling down the solution to conduct the natural crystallization and further filtering out in a short time, the mixture of the α-type crystals and the θ-type crystals is obtained.)

2.01 g of thus obtained mixture of the α-type crystals and the θ-type crystals of the compound of the formula (I) was added to 11 mL of the acetonitrile-dimethylformamide (4:1 volume ratio) and stirred at 60° C. for 3 hours. The precipitated crystals of the suspension was collected by filtration at 60° C. and dried at 60° C. under reduced pressure to obtain 1.42 g of the title crystals (yield: 71%).

Example 30

The Crystallization by Suspension (the θ-type Crystal).

20.04 g of the compound of the formula (I), which is a solid mainly comprising the α-type crystals was added to 220 mL of acetonitrile-water (9:1 volume ratio) and stirred by heating at 61° C. Ig of the θ-type crystals was added thereto and continuously heated at 60° C. for 24 hours. At that time, the partial pullout of the suspension was conducted three times in order to check the crystal form (total of 8.71 g of the crystals was pulled out). The precipitated crystals were collected by filtration at 60° C. and dried under reduced pressure to obtain 5.06 g of the title crystals.

Example 31

The Crystallization by Suspension (the θ-type Crystal).

The compound of the formula (I) comprising 2.01 g of the α-type crystals and 1.72 g of the θ-type crystals was added to 100 g of acetonitrile-water (1:1 volume ratio) and stirred at 40° C. for 95 hours. At that time, the partial pullout of the suspension was conducted twice in order to check the crystal form (total of 1.84 g of the crystals were pulled out). The precipitated crystals were collected by filtration at 40° C. and dried under reduced pressure to obtain 1.46 g of the title crystals.

Analytic Example 1

Measurement of Powder X-ray Diffraction Patterns
(1) The measuring method and conditions
  Target: Cu Full automatic monochromator
  Voltage: 40 kV
  Current: 40 mV
  Slit: divergence ½°
    scattering ½°
    light receiving 0.15 mm
  Scan Speed: 2°/min.
  2θ range: 3 to 30°
(2) The measurement results FIGS. 1 to 5 show the powder X-ray diffraction patterns of the α-type, γ-type, ε-type, η-type, and θ-type crystals, respectively.

Besides, Tables 1 to 5 show the diffraction angles (2θ) of the main peaks and the strength of each of the crystals.

TABLE 1

| α-type | |
|---|---|
| 2θ | strength |
| 6.2 | strong |
| 10.2 | strong |
| 10.7 | strong |
| 10.8 | strong |
| 14.0 | strong |
| 14.4 | strong |
| 16.0 | strong |
| 16.2 | strong |
| 17.1 | medium |
| 17.2 | medium |
| 18.4 | medium |
| 18.8 | medium |
| 20.6 | medium |
| 21.7 | strong |
| 23.1 | medium |
| 27.8 | medium |
| 28.1 | medium |

TABLE 2

| γ-type | |
|---|---|
| 2θ | strength |
| 7.2 | medium |
| 8.1 | strong |
| 10.3 | medium |
| 10.9 | medium |
| 14.5 | medium |
| 15.1 | medium |
| 16.4 | medium |
| 17.3 | medium |
| 18.3 | medium |
| 19.4 | medium |
| 20.1 | medium |
| 20.7 | medium |
| 21.4 | medium |
| 23.3 | strong |
| 23.9 | medium |

TABLE 3

| ε-type | |
|---|---|
| 2θ | strength |
| 5.4 | medium |
| 6.9 | medium |
| 8.3 | medium |
| 10.8 | strong |
| 11.1 | strong |
| 12.8 | strong |
| 16.1 | medium |
| 16.4 | medium |
| 17.7 | medium |
| 21.6 | strong |
| 23.4 | strong |

TABLE 3-continued

| ε-type | |
|---|---|
| 2θ | strength |
| 24.5 | strong |
| 25.1 | strong |

TABLE 4

| η-type | |
|---|---|
| 2θ | strength |
| 9.7 | strong |
| 12.2 | strong |
| 12.8 | medium |
| 14.9 | medium |
| 15.6 | medium |
| 16.9 | medium |
| 18.5 | strong |
| 20.4 | strong |

TABLE 5

| θ-type | |
|---|---|
| 2θ | strength |
| 5.7 | medium |
| 10.3 | medium |
| 11.5 | strong |
| 13.9 | strong |
| 16.5 | medium |
| 18.5 | strong |
| 20.0 | strong |
| 21.0 | strong |
| 21.9 | medium |
| 23.0 | medium |
| 26.0 | medium |

The compound described in Example 196 of WO02/16329 (Patent Literature 1) is explained as follows as a comparative example.

Comparative Example 1

The compound described in Example 196 of Patent Literature 1 is the compound synthesized in accordance with Example 196 of Patent Literature 1 and that obtained as a hydrochloride was used.

Figure 6:
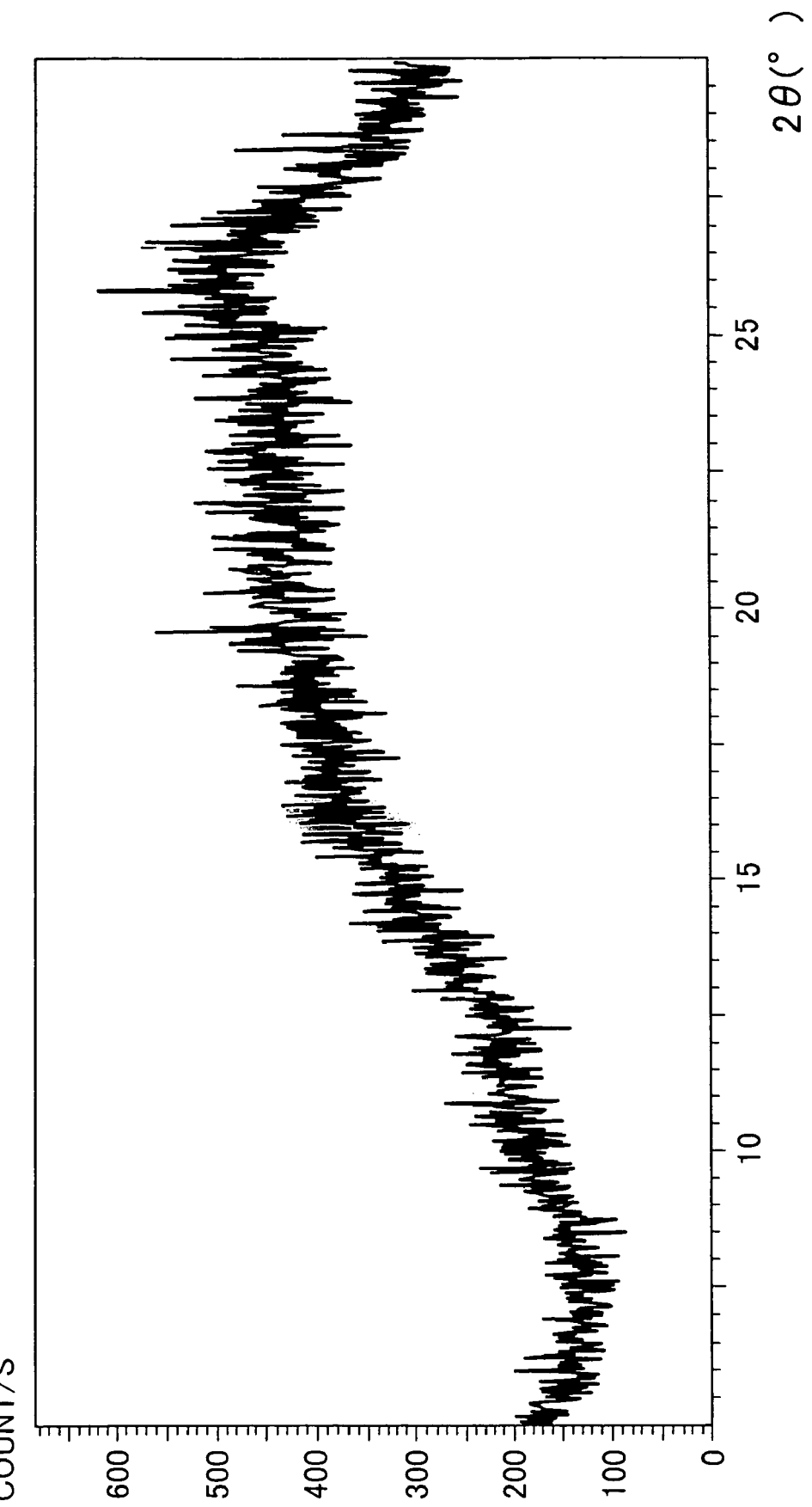
FIG. 6 is a powder X-ray diffraction pattern of the known compound (a hydrochloride of the compound of the formula (I)) indicated in Comparative Example 1. The horizontal axis indicates the diffraction angle 2θ (°); and the vertical axis indicates the strength (counts per second, CPS).

It is clarified from the result of the powder X-ray diffraction in FIG. 6 that the compound is amorphous.

Analytic Example 2

Figure 7:
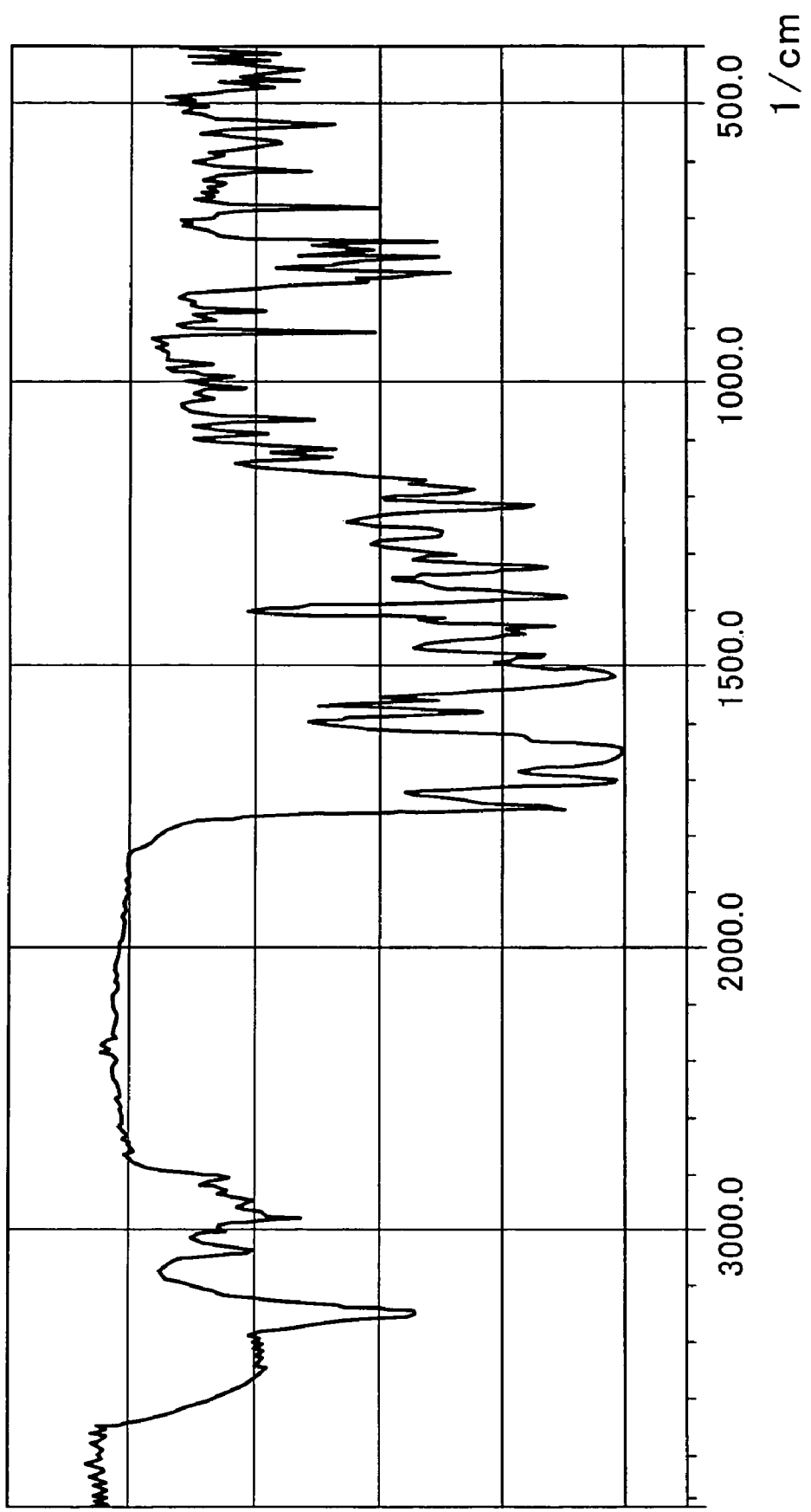
FIG. 7 is an infrared absorption spectrum of the α-type crystal.

Measurement of the Infrared Absorption Spectrum
(1) The measuring method and conditions
The infrared absorption spectrum was measured by FT-IR in accordance with the potassium bromide disk method in the General Tests of the Japanese Pharmacopoeia.
(2) The measurement results
FIG. 7 shows the infrared absorption spectrum of the α-type crystal.

Test Examples

Test Examples will further illustrate the effects of the present invention.

The thermodynamically stable crystal forms were confirmed by Test Examples 1 and 2. Similarly, the crystal forms having low hygroscopicity were confirmed by Test Example 3.

Test Example 1

Figure 8:
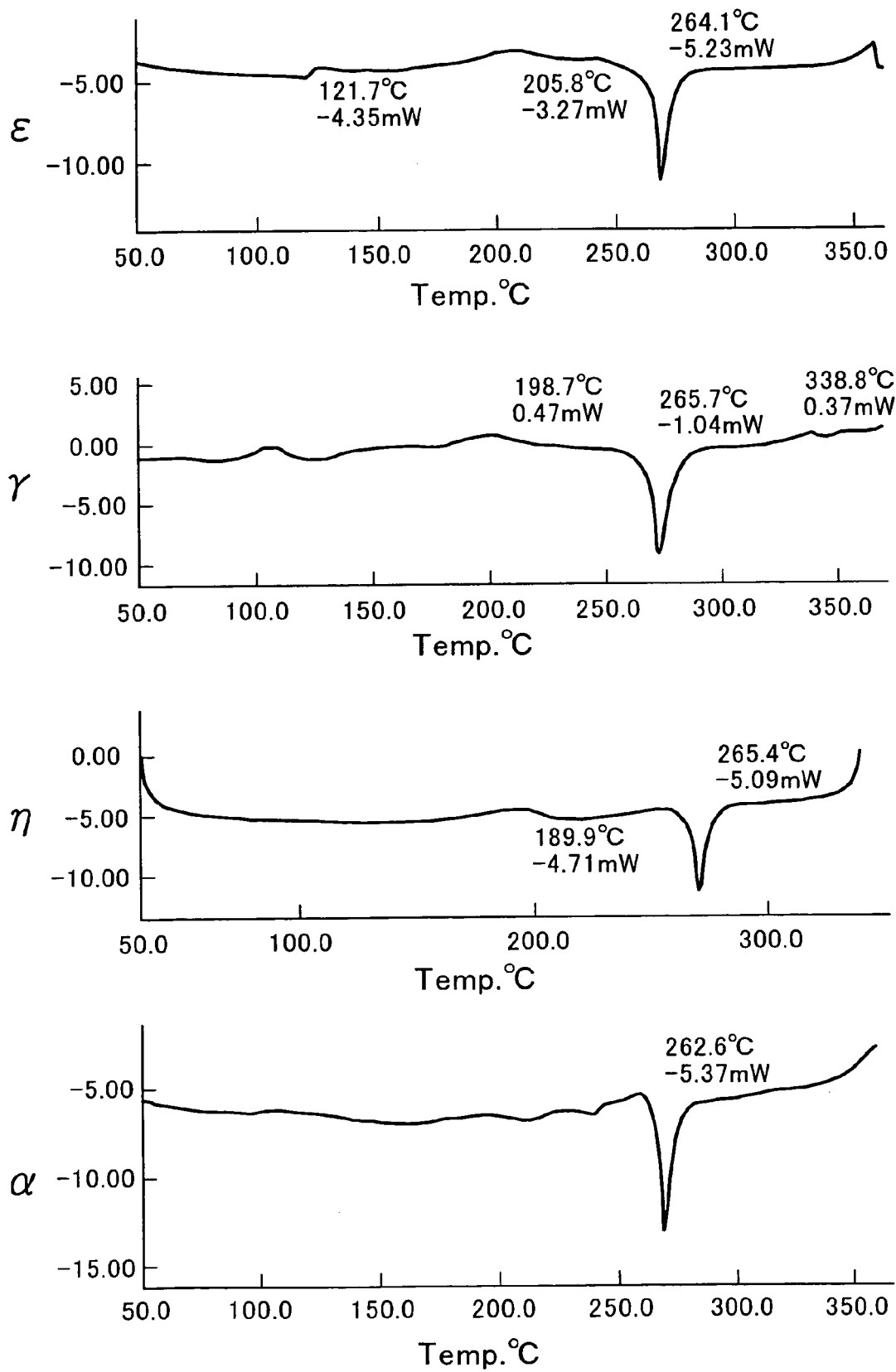
FIG. 8 shows the DSC patterns of the α-type, γ-type, ε-type, and η-type crystals.

Differential Scanning Calorimetry: DSC
(1) The measuring method and conditions
1 to 7 mg of the samples of each of the above obtained crystal forms (α-type, γ-type, ε-type and η-type) were weighed and sealed in the aluminum pan. Then, DSC was conducted in the following conditions.
Reference: An empty aluminum pan
Scan Speed: 10° C./min.
Sampling time: 0.2 sec.
Range: 50 to 350° C.
(2) The measurement results
FIG. 8 shows the DSC patterns of the α-type, γ-type, ε-type, and η-type crystals.

It was observed by DSC that all of the α-type, γ-type, ε-type, and η-type crystals have the endothermic peak at around 265° C. The measurement of the melting points by the visual observation determined the each melting point of the α-type, γ-type, ε-type, and η-type crystals at around 257 to 264° C.

Test Example 2

Figure 9:
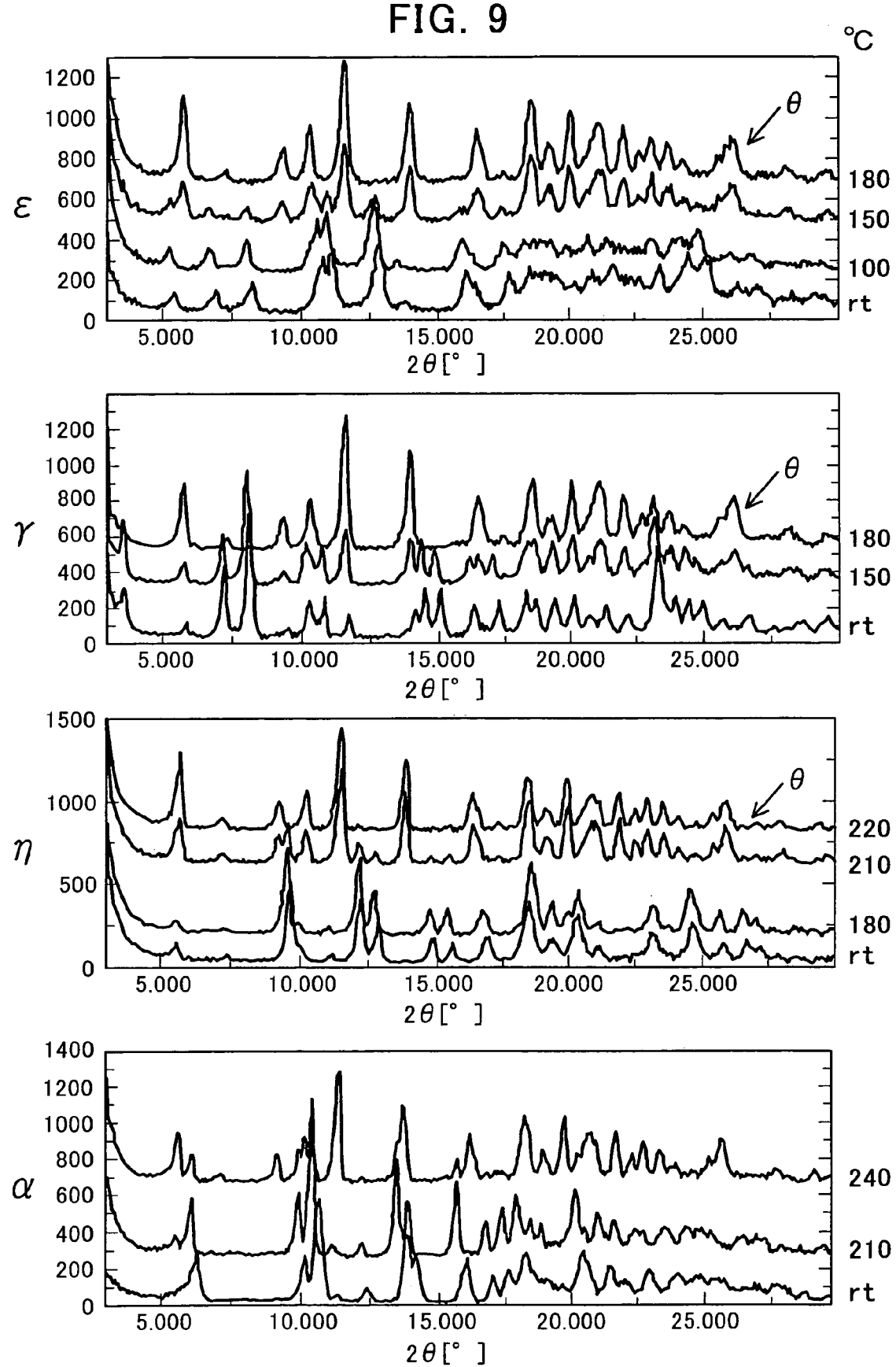
FIG. 9 shows the effect of temperature change on the powder X-ray diffraction patterns of the α-type, γ-type, ε-type, and η-type crystals.

Measurement of the Temperature Changes of the Powder X-ray Diffraction Patterns of the α-type, γ-type, ε-type, and η-type Crystals
(1) The measuring method and conditions
The measurement was conducted in the same conditions as those of the above measurement of the powder X-ray diffraction patterns.
Meanwhile, in order to change the temperature, the desired temperature was set by the temperature control unit.
(2) The measurement results
FIG. 9 shows the temperature changes of the powder X-ray diffraction patterns of the α-type, γ-type, ε-type, and η-type crystals.

All of the α-type, γ-type, ε-type, and η-type crystal forms changed to new crystal form patterns (corresponding to the θ-type crystal in the present specification) on the high temperature side by the temperature change. It was thought that the reason why all of the crystal forms had the melting point at around 265° C. in Test Example 1 was the melting point of the θ-type crystal.

The transition temperature from the α-type crystal to the θ-type crystal was seen at 230° C. or higher and 250° C. or lower; that from the γ-type crystal to the θ-type crystal was seen at 160° C. or higher and 200° C. or lower; that from the ε-type crystal to the θ-type crystal was seen at 150° C. or higher and 200° C. or lower; and that from the η-type crystal to the θ-type crystal was seen at 210° C. or higher and 230° C. or lower.

Figure 10:
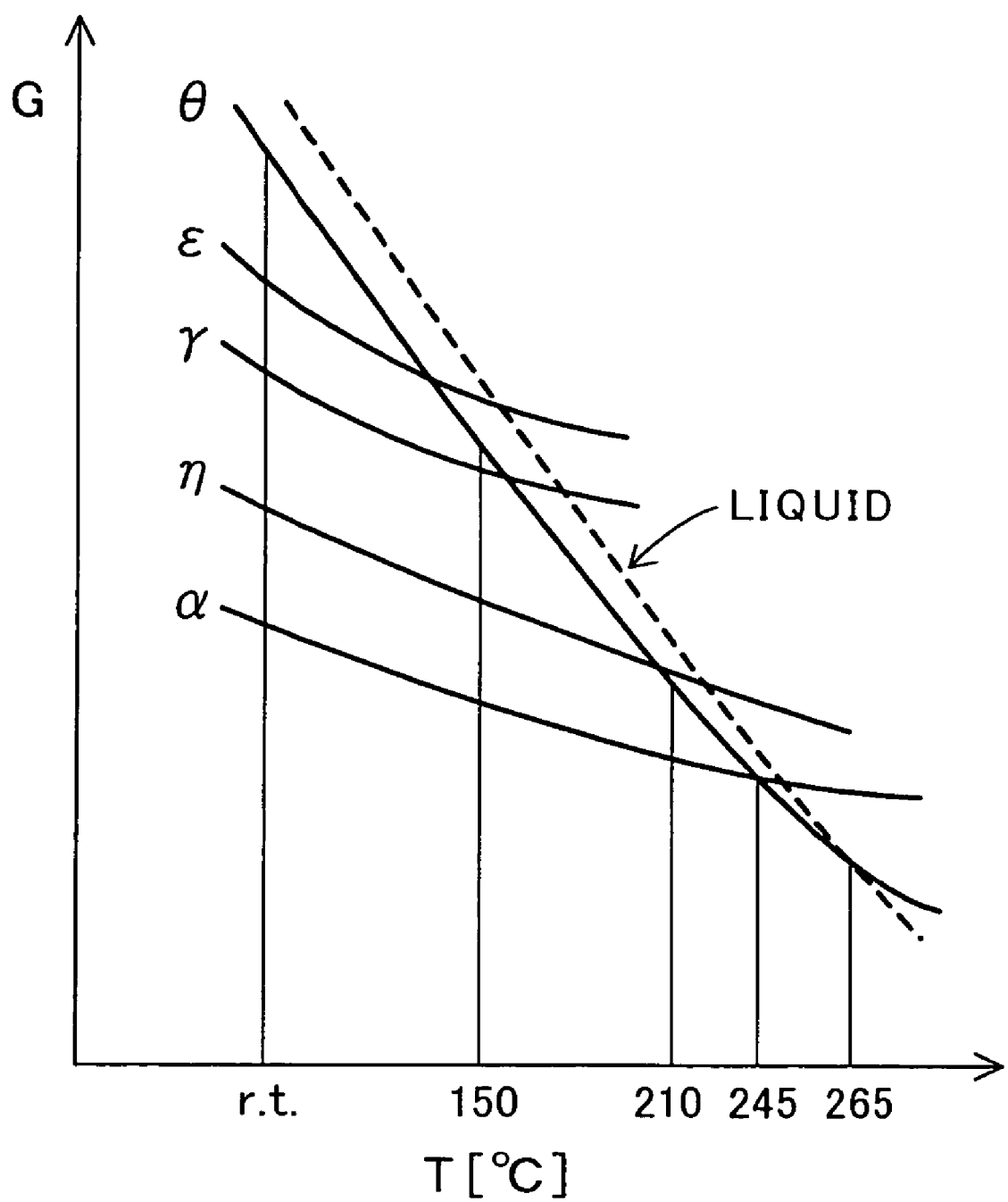
FIG. 10 shows the T-G curves (T: temperature (° C.), G: the relative value of Gibbs free energy) of the α-type, γ-type, ε-type, η-type, and θ-type crystals.

The T-G curves (T: temperature (° C.), G: the relative value of Gibbs free energy) of the α-type, γ-type, ε-type, η-type, and θ-type crystals were indicated from the above results (refer to FIG. 10).

From FIG. 10, it is thought that the thermodynamically stable crystal form at room temperature is the α-type crystal and α-type>η-type>γ-type>ε-type>θ-type in that order. Meanwhile, when the crystal transition occurs in high temperature range, it is thought that the θ-type crystal is generated and stably exists.

Test Example 3

The Measuring Method of the Water Adsorption of the Crystals (Creation of the Vapor Adsorption Isotherm)

(1) The measuring method of water adsorption amount and conditions 100 mg of each of the above obtained α-type, γ-type and ε-type crystals were weighed and vacuum dried at 50° C. overnight. Then, under the constant temperature of 25° C., the water adsorption amount of the crystals was determined with a full automatic vapor adsorption measuring apparatus (BEL-SORP-18, BEL Japan, Inc.) (Mitsuiki et al., *J. Agric. Food Chem.*, vol. 46, no. 9, pp. 3528-3534 (1998)).

(2) The measurement results

Figure 11:
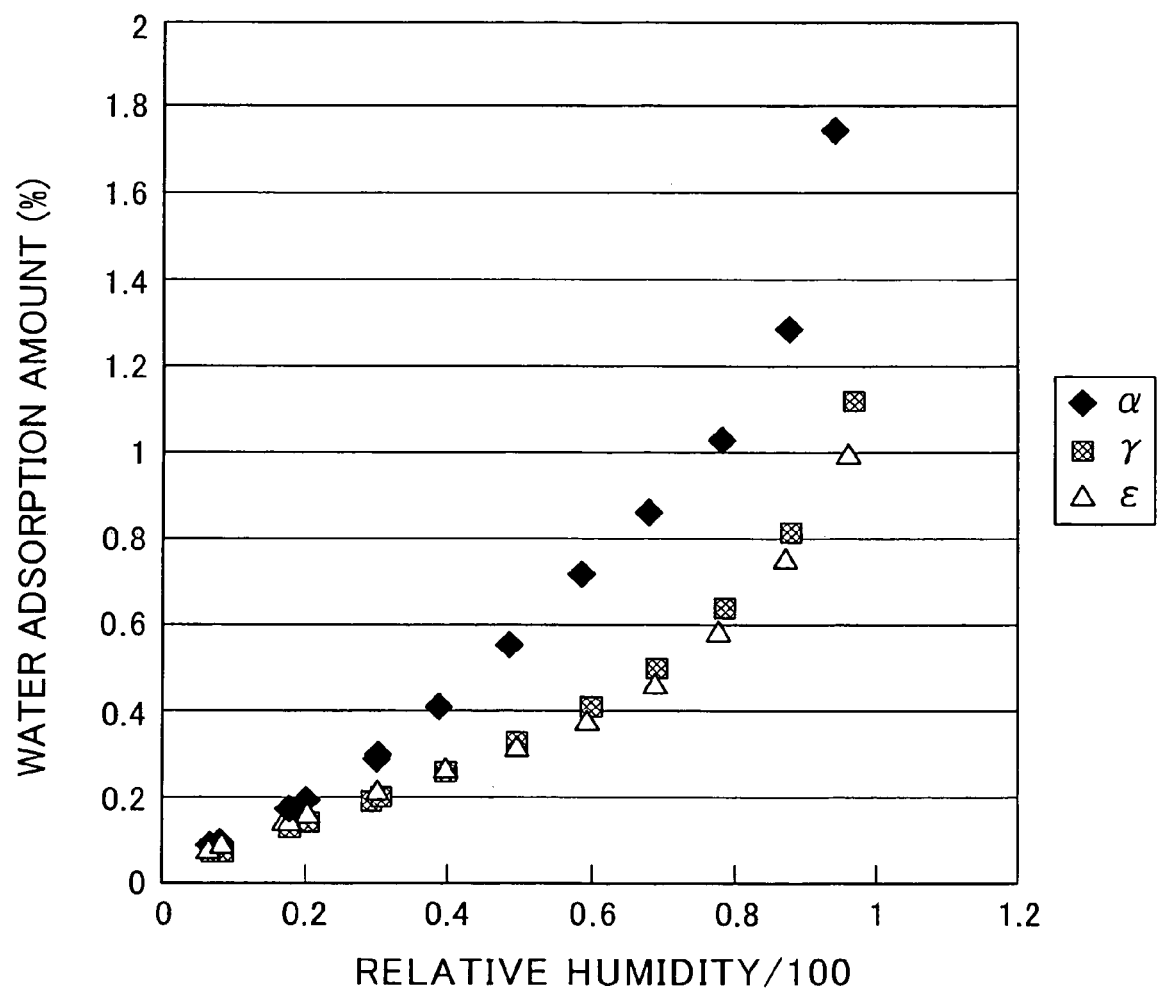
FIG. 11 shows the vapor adsorption isotherms of the α-type, γ-type, and ε-type crystals. The horizontal axis indicates the relative humidity (%)/100; and the vertical axis indicates the water adsorption amount (%).

FIG. 11 shows the vapor adsorption isotherm of the α-type, γ-type and ε-type crystals. The horizontal axis indicates the relative humidity (%)/100; and the vertical axis indicates the water adsorption amount (%).

All of the α-type, -γ-type and ε-type crystals have the water adsorption amount of 2% or lower even in the relative humidity of 100%. Therefore, it is seen that they have low water adsorption and the ε-type and γ-type crystals have particularly low water adsorption.

Figure 12:
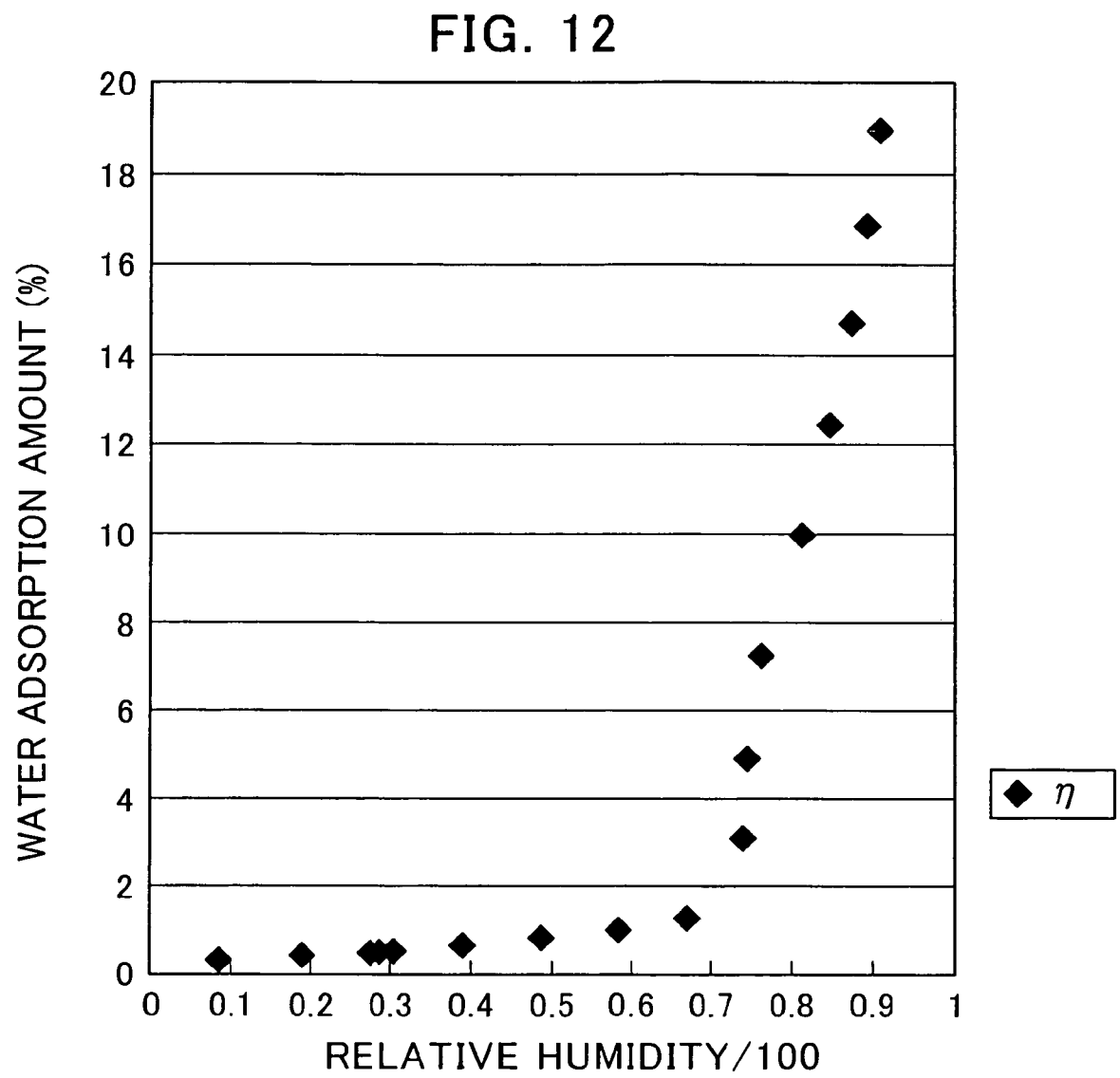
FIG. 12 shows the vapor adsorption isotherm of the η-type crystal. The horizontal axis indicates the relative humidity (%)/100; and the vertical axis indicates the water adsorption amount (%).

For reference, FIG. 12 shows the vapor adsorption isotherm of the η-type crystal. The horizontal axis indicates the relative humidity (%)/100; and the vertical axis indicates the water adsorption amount (%).

The present invention provides the crystals excellent in preservation stability or moisture resistance of drug substances or preparations; or those that can be produced on the industrial scale. The compounds having the crystal forms of the present invention have an α4 integrin inhibiting activity, and are useful as therapeutic agents or preventive agents for diseases in which α4 integrin-depending adhesion process participates in the pathology, such as inflammatory diseases, rheumatoid arthritis, inflammatory bowel diseases, systemic erythematodes, multiple sclerosis, Sjogren's syndrome, asthma, psoriasis, allergy, diabetes, cardiovascular diseases, arterial sclerosis, restenosis, tumor proliferation, tumor metastasis and transplantation rejection.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A crystal of the compound of formula (I):

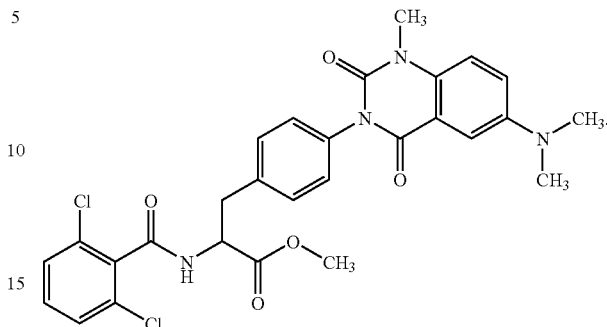

which is an α-type crystal which exhibits peaks at the diffraction angles (2θ) of at least 6.2°, 10.7°, and 14.0° in the powder X-ray diffraction pattern.

2. A crystal according to claim 1, which exhibits peaks at the diffraction angles (2θ) of at least 6.2°, 10.7°, 10.8°, 14.0°, 16.2°, and 21.7° in the powder X-ray diffraction pattern.

3. A crystal according to claim 1, which exhibits peaks at the diffraction angles (2θ) of at least 6.2°, 10.2°, 10.7°, 10.8°, 14.0°, 14.4°, 16.0°, 16.2°, and 21.7° in the powder X-ray diffraction pattern.

4. A method for producing an α-type crystal according to claim 1, which comprises dissolving the compound of the formula (I) in a solvent which comprises at least one solvent selected from the group consisting of acetonitrile, dichloromethane, tetrahydrofuran, acetone, dimethylsulfoxide and chloroform, or in a mixed solvent of acetonitrile-water, or in a mixed solvent of acetonitrile dimethylformamide, to obtain a mixture; and cooling the mixture to 0 to 30° C. to obtain said crystal.

5. A method for producing an α-type crystal according to claim 1, which comprises dissolving the compound of the formula (I) in a first solvent to obtain a mixture; and then adding a second solvent to said mixture to obtain said crystal, wherein the combination of said first solvent and said second solvent is selected from the group consisting of dimethylsulfoxide and toluene; dimethylformamide and diethylether; dimethylformamide and toluene; chloroform and ethanol; chloroform and toluene; chloroform and diethylether; dichloromethane and diethylether; tetrahydrofuran and water; tetrahydrofuran and cyclohexane; acetone and water; acetonitrile and water; and dimethylformamide and acetonitrile.

6. A method for producing an α-type crystal according to claim 1, which comprises suspending the compound of formula (I) in acetonitrile, a mixed solvent of acetonitrile-water, or a mixed solvent of acetonitrile-dimethylformamide, to obtain a mixture; and stirring the mixture at 0 to 40° C. to obtain said crystal.

7. The method of claim 4, wherein said mixture is cooled to 4 to 25° C. to obtain said crystal.

8. A method for producing an α-type crystal according to claim 2, which comprises dissolving the compound of the formula (I) in a solvent which comprises at least one solvent selected from the group consisting of acetonitrile, dichloromethane, tetrahydrofuran, acetone, dimethylsulfoxide and chloroform, or in a mixed solvent of acetonitrile-water, or in a mixed solvent of acetonitrile-dimethylformamide, to obtain a mixture; and cooling the mixture to 0 to 30° C. to obtain said crystal.

9. The method of claim 8, wherein said mixture is cooled to 4 to 25° C. to obtain said crystal.

10. A method for producing an α-type crystal according to claim 2, which comprises dissolving the compound of the formula (I) in a first solvent to obtain a mixture; and then adding a second solvent to said mixture to obtain said crystal, wherein the combination of said first solvent and said second solvent is selected from the group consisting of dimethylsulfoxide and toluene; dimethylformamide and diethylether; dimethylformamide and toluene; chloroform and ethanol; chloroform and toluene; chloroform and diethylether; dichloromethane and diethylether; tetrahydrofuran and water; tetrahydrofuran and cyclohexane; acetone and water; acetonitrile and water; and dimethylformamide and acetonitrile.

11. A method for producing an α-type crystal according to claim 2, which comprises suspending the compound of formula (I) in acetonitrile, a mixed solvent of acetonitrile-water, or a mixed solvent of acetonitrile-dimethylformamide, to obtain a mixture; and stirring the mixture at 0 to 40° C. to obtain said crystal.

12. A method for producing an α-type crystal according to claim 3, which comprises dissolving the compound of the formula (I) in a solvent which comprises at least one solvent selected from the group consisting of acetonitrile, dichloromethane, tetrahydrofuran, acetone, dimethylsulfoxide and chloroform, or in a mixed solvent of acetonitrile-water, or in a mixed solvent of acetonitrile-dimethylformamide, to obtain a mixture; and cooling the mixture to 0 to 30° C. to obtain said crystal.

13. The method of claim 12, wherein said mixture is cooled to 4 to 25° C. to obtain said crystal.

14. A method for producing an α-type crystal according to claim 3, which comprises dissolving the compound of the formula (I) in a first solvent to obtain a mixture; and then adding a second solvent to said mixture to obtain said crystal, wherein the combination of said first solvent and said second solvent is selected from the group consisting of dimethylsulfoxide and toluene; dimethylformamide and diethylether; dimethylformamide and toluene; chloroform and ethanol; chloroform and toluene; chloroform and diethylether; dichloromethane and diethylether; tetrahydrofuran and water; tetrahydrofuran and cyclohexane; acetone and water; acetonitrile and water; and dimethylformamide and acetonitrile.

15. A method for producing an α-type crystal according to claim 3, which comprises suspending the compound of formula (I) in acetonitrile, a mixed solvent of acetonitrile-water, or a mixed solvent of acetonitrile-dimethylformamide, to obtain a mixture; and stirring the mixture at 0 to 40° C. to obtain said crystal.

* * * * *